(12) United States Patent
Markham

(10) Patent No.: US 6,641,830 B1
(45) Date of Patent: Nov. 4, 2003

(54) DEER REPELLENT

(76) Inventor: Christopher John Markham, 366 Sparta Ave., Sparta, NJ (US) 07871

( * ) Notice: Subject to any disclaimer, the term of this patent is extended or adjusted under 35 U.S.C. 154(b) by 0 days.

(21) Appl. No.: 10/233,346

(22) Filed: Sep. 3, 2002

(51) Int. Cl.⁷ .............................................. A01N 25/32
(52) U.S. Cl. .................... 424/406; 424/405; 424/407; 426/1; 426/2; 514/517; 514/920
(58) Field of Search ................. 514/517, 920; 426/1, 2; 424/405, 406, 407

(56) References Cited

U.S. PATENT DOCUMENTS

| | | | | |
|---|---|---|---|---|
| 3,937,826 A | * | 2/1976 | Harris | |
| 3,980,773 A | * | 9/1976 | Oh | |
| 3,996,349 A | * | 12/1976 | Mulla et al. | |
| 4,735,803 A | * | 4/1988 | Katz et al. | |
| 5,183,661 A | * | 2/1993 | Messina | 424/405 |
| 6,001,874 A | * | 12/1999 | Veierov | |

* cited by examiner

Primary Examiner—Neil S. Levy

(57) ABSTRACT

A deer repellent to deter deer from eating trees, shrubs and plants. The deer repellent is a mixture of milk, eggs, corn oil and sodium lauryl sulfate. The mixture is blended and applied to the foliage with a sprayer to prevent unwanted deer browse.

2 Claims, No Drawings

DEER REPELLENT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING

Not Applicable

BACKGROUND OF THE INVENTION (0001) Deer browse in New Jersey is a large problem for many homeowners, landscapers and landscape architects. As a small business owner and wildlife biologist, I believe that if I could mix a spray that could be applied to the plant, shrub or tree that would deter the deer from eating its foliage, I could help solve many of the problems encountered by the previously mentioned individuals.

(0002) Many deer repellents exist on the market. Most only deter the deer for a very short time, while others are offensive to smell. Furthermore, most need to be applied on a constant basis, depending on the weather or watering schedule, and are inconvenient for the user.

(0003) As a small business, only products exempted by the Environmental Protection Agency could be used, due to the high costs and lengthy process of the pesticide registration process. After experimenting with many mixes, a combination of milk, eggs, corn oil and sodium lauryl sulfate worked the best, and stayed within the Environmental Protection Agency guidelines.

(0004) Once I settled on a solution (0003), I conducted an experiment two different times. Plots of plants were put in a heavy deer browse area, and divided into separate groups. Some groups were sprayed with my formula (0003), some were sprayed with commercial brands, and some were left as controls and sprayed with nothing at all. All plots were sprayed only once and were watered on the same schedule. The controls were immediately eaten within a day or two, while most commercial brands were eaten within a week. My formula lasted over 2 months, with only new growth being lightly browsed after the first month.

(0005) My formula can allow homeowners, landscapers and landscape architects more freedom in their choice of plants and designs. When applied on a monthly basis, the spray can eliminate many of the browse problems caused by deer.

BRIEF SUMMARY OF THE INVENTION (0006) Frustration and unwanted spending is encountered by homeowners as well as landscape professionals throughout New Jersey because of the browse damage caused by the heavy concentration of deer.

(0007) A mix of milk, eggs, corn oil and sodium lauryl sulfate was used by myself in experiments to combat the deer browse problem. The formula was spread through a sprayer and compared to other commercial brands as part of a experiment.

(0008) The mix (0007) was not only odorless, unlike many other commercial brands, but it lasted longer, up to and over 2 months in some cases.

(0009) The formula, which is exempt for pesticide registration by the Environmental Protection Agency, when properly applied, can be used to help eliminate unwanted deer browse.

BRIEF DESCRIPTION OF SEVERAL VIEWS OF THE DRAWING

Not Applicable

DETAILED DESCRIPTION OF THE INVENTION (0010) The deer repellent formula consists of milk (60.87%), eggs (30.43%), corn oil (4.35%) and {28 percent} 29 percent aqueous solution sodium lauryl sulfate (4.35%).

(0011) The ingredients go into a blender and are properly mixed.

(0012) The formula is the transferred into a sprayer, where a light-medium mist is recommended be applied to the foliage and flowers.

(0013) Within a few hours, the formula is dry and a regular watering schedule can be resumed.

(0014) The formula can last over 2 months, although it is recommended new growth be sprayed once a month.

What is claimed is:

1. A composition for deer repellent consisting essentially of 60.87% milk, 30.43% deshelled chicken eggs, 4.35% corn oil and 4.35% of a 29 percent aqueous solution of sodium lauryl sulfate, the percentages based on volume of the total composition, which are blended together to form a uniform composition effective to repel deer.

2. A method of repelling deer, the blended composition of claim 1 applied through a sprayer to form a light/medium mist on the foliage of flowers, plants, shrubs and trees in an amount to deter deer from browsing the foliage.

* * * * *